United States Patent
Haras

(10) Patent No.: US 8,182,149 B2
(45) Date of Patent: May 22, 2012

(54) METHOD AND MARKING OUT APPARATUS FOR MARKING OUT A GUIDE LINE FOR A PENETRATION INSTRUMENT, CONTROL DEVICE AND RECORDING SYSTEM

(75) Inventor: Gabriel Haras, Mücke (DE)

(73) Assignee: Siemens Aktiengesellschaft, Munich (DE)

( * ) Notice: Subject to any disclaimer, the term of this patent is extended or adjusted under 35 U.S.C. 154(b) by 587 days.

(21) Appl. No.: 12/382,172

(22) Filed: Mar. 10, 2009

(65) Prior Publication Data

US 2009/0234370 A1    Sep. 17, 2009

(30) Foreign Application Priority Data

Mar. 11, 2008 (DE) .......................... 10 2008 013 615

(51) Int. Cl.
*A61B 6/08* (2006.01)
(52) U.S. Cl. ........................................ 378/206; 378/205
(58) Field of Classification Search .................... 378/65, 378/206, 205
See application file for complete search history.

(56) References Cited

U.S. PATENT DOCUMENTS

| | | | |
|---|---|---|---|
| 5,782,842 A * | 7/1998 | Kloess et al. | ................. 606/130 |
| 6,041,249 A | 3/2000 | Regn | |
| 6,443,960 B1 | 9/2002 | Bendiksen | |
| 2007/0036274 A1 | 2/2007 | Aulbach | |
| 2008/0013678 A1 | 1/2008 | Magerl et al. | |

FOREIGN PATENT DOCUMENTS

| | | |
|---|---|---|
| DE | 19801446 A1 | 9/1998 |
| DE | 102005030285 B4 | 4/2007 |

OTHER PUBLICATIONS

Office Action for German patent application No. 10 2008 013 615.8 dated Apr. 7, 2011.

* cited by examiner

*Primary Examiner* — Hoon Song
(74) *Attorney, Agent, or Firm* — Harness, Dickey & Pierce, P.L.C.

(57) ABSTRACT

A method is disclosed for marking out a guide line of a penetration instrument entering an object along a penetration channel. In at least one embodiment, the penetration channel into the object is firstly determined based on image data of the object generated by an imaging recording system, the penetration channel being defined by a penetration point into the object and at least one penetration direction. Then, at least two light fan beams are emitted from different directions in such a fashion that the line of intersection of the fan beams is coaxial with the penetration direction. A marking out apparatus is further disclosed for carrying out the method, along with a control device suitable to this end, and an imaging recording system including such a marking out apparatus.

20 Claims, 5 Drawing Sheets

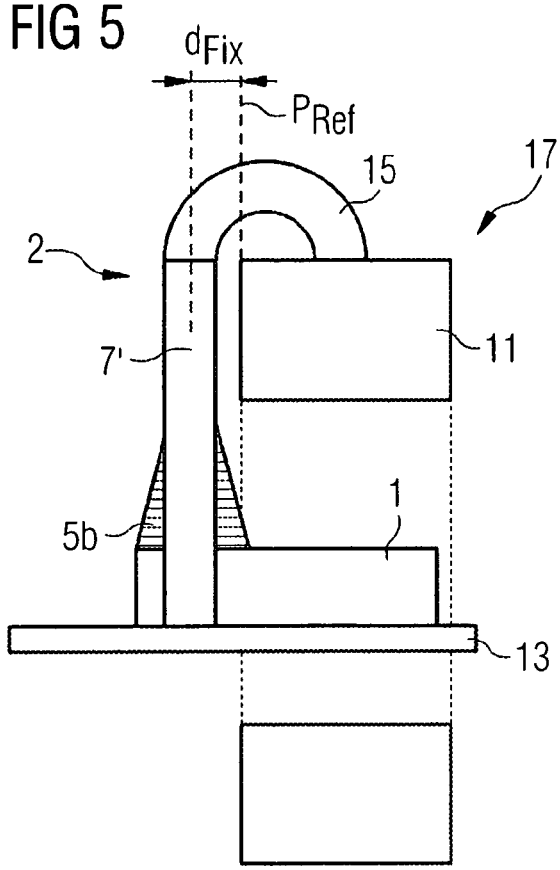
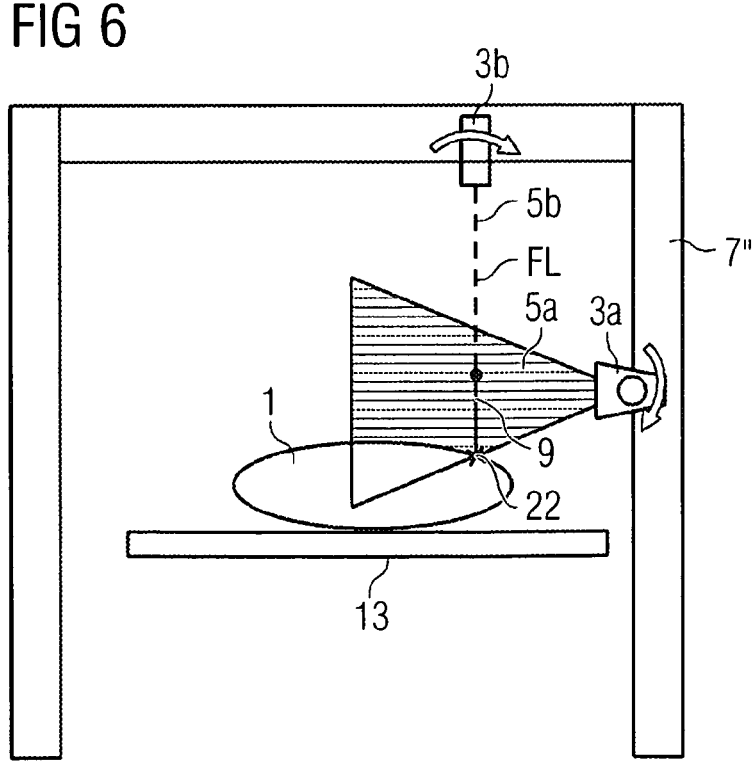

METHOD AND MARKING OUT APPARATUS FOR MARKING OUT A GUIDE LINE FOR A PENETRATION INSTRUMENT, CONTROL DEVICE AND RECORDING SYSTEM

PRIORITY STATEMENT

The present application hereby claims priority under 35 U.S.C. §119 on German patent application number DE 10 2008 013 615.8 filed Mar. 11, 2008, the entire contents of which is hereby incorporated herein by reference.

FIELD

At least one embodiment of the present invention generally relates to a method for marking out a guide line for a penetration instrument entering an object along a penetration channel. At least one embodiment of the invention also generally relates to a marking out apparatus with light emission sources, a control device for actuating light emission sources, which emit at least two light beams, of such a marking out apparatus, and/or an imaging recording system comprising such a marking out apparatus.

BACKGROUND

In order to determine guide lines of penetration instruments in objects, it is often the case that an imaging method is firstly used to image the object which is intended to be penetrated by the penetration instrument and, if possible, determine prominent points within the object. For example, within the scope of so-called CT intervention, a computed tomography system can be used to make visible a tumor inside an organ of a patient, which tumor is intended to be ablated or extracted with the aid of an endoscopic instrument, or from which tissue samples are intended to be taken within the scope of a tumor biopsy. In the process, the location of tissue structures which should not be injured by the instrument, for example sensitive, healthy organs, is also made visible by the image data generated by the computed tomography system.

Such targeted penetration of a penetration instrument entering an object may also be necessary in very different applications, not all of which are in the field of medical technology. Firstly, the imaging method carries out non-invasive imaging, which makes it possible to identify a particular target object and provide the user of the penetration instrument with coordinates by way of which the instrument can be inserted into the object in a targeted manner so it can reach the respective location with the smallest amount of risk.

However, simple availability of the coordinates from the imaging method does not yet guarantee that a user can carry out such a penetration in a precise and targeted manner. Rather, to this end, it is necessary to mark out a guide line for the penetration instrument. Preferably, this occurs with the aid of automated marking out methods. To this end, DE 10 2005 030285 B4 proposes to use a marking out device which fixedly irradiates an intervention position with the aid of a laser beam. DE 198 01 446 A1 also discloses such a laser marking out, with the laser light source used for this purpose being displaceable along a rail.

Furthermore, U.S. Pat. No. 5,782,842 discloses marking out a guide line with the aid of two differently colored light beams, in particular using fan light beams. This guide line is defined by an entry point and an entry angle. However, it is often the case that the initial entry point and entry angle cannot be maintained during the insertion of the instrument, for example because the instrument would encounter, at a particular location within the object, regions which it cannot touch or which prevent it from further progress. In this respect, U.S. Pat. No. 5,782,842, using the light beam marking out, only represents a first starting point, from where and at what angle a user should firstly apply the instrument.

SUMMARY

In at least one embodiment of the present invention, an improved and effective method is provided for marking out a guide line for a penetration instrument entering an object, and, furthermore, an accordingly designed marking out apparatus and a corresponding control device are also provided.

According to at least one embodiment of the invention, a method is disclosed for marking out a guide line for a penetration instrument entering an object along a penetration channel, comprising:

determining the penetration channel into the object based on image data, preferably volume image data, of the object generated by an imaging recording system, for example a computed tomography system, the penetration channel being defined by a penetration point into the object and at least one penetration direction, and emitting at least two light fan beams from different directions so that the line of intersection of the fan beams is coaxial with the penetration direction, wherein measurement data for determining the position of the penetration instrument is acquired by the imaging recording system and the alignment of the fan beams is corrected depending on a position of the penetration instrument as determined by determining the position of the penetration instrument.

Within the scope of embodiments of this method, it is possible that the image data of the object also refers to parts of the object. The penetration object is preferably elongate and preferably has a straight design; for example, it is designed as a catheter, needle or cannula. It is usual for the light fan beams to originate from different directions and different light emission sources. In the following text, the term "light emission sources" is understood to include all objects or surfaces which radiate light. These can include light sources which automatically emit light and also other surfaces or points which radiate light. For example, these include those light emission sources which emit light generated at another location or which are used as optical deflection and/or diffusion points, such as the ends of optical waveguides into which laser light is fed, or mirrors, prisms or apparatuses with lenses.

Preferably, fanned laser beams are used as light fan beams. Light which is visible to the human eye is used, preferably having a red coloring which can be recognized particularly well so that the line of intersection of the fan beams is visible to the human eye at least when an object is located in the beam path. This line of intersection marks out the guide direction of the penetration instrument.

Using fan beams instead of punctiform beams for marking out the guide line of the penetration instrument significantly increases the visibility of this guide line to a user. To be precise, while one or more punctiform light beams show points on the object or lines in space, fan beams can usually be recognized much more easily by the human eye. Within the scope of embodiments of the invention, fan beams are understood to be those beams from a light emission source which either comprise a plurality of approximately punctiform beams arranged along a surface or which generate a largely homogeneous radiation surface. This radiation surface is preferably of planar design. Using two such fan beams makes it possible to generate a common line of intersection which, according to embodiments of the invention, marks out the guide line of the penetration instrument. If a penetration instrument is now placed precisely onto the line of intersection of the two light fan beams, it is thus aligned with the penetration direction of the envisaged penetration channel. The penetration instrument must now be guided along this line of intersection in the direction of the object and hence reaches its penetration point.

Furthermore, the imaging recording system also acquires measurement data to determine the position of the penetration instrument. As a result of this, the object and the penetration instrument can advantageously be imaged using the same method and it is possible to determine their positions with respect to one another. Advantageously, the alignment of the fan beams is then corrected depending on a position of the penetration instrument as determined by determining the position of the penetration instrument.

During penetration into the object, the alignment of the fan beams can be corrected depending on the guide line. Thus, if the optimum penetration channel does not lie along a straight line but rather changes direction, or even bends, along its profile in the object, it is possible to ensure that even during the penetration procedure the optimum penetration channel is followed by changing the guide line by correspondingly correcting the light fan beams. Since visible light fan beams are used, this correction can easily be seen by the user.

By comparing this to the prior art, the advantages of an accordingly designed method become apparent:

Whilst up until now a penetration instrument had to be placed such that a punctiform marking beam fell directly onto the back end of the penetration instrument and that the penetration instrument was aligned as an extension of this marking beam, the line of intersection of the two fan beams can now make this penetration direction clearly visible in space so that a user now only has to bring the penetration instrument directly onto this line of intersection. The alignment of the fan beams is then corrected depending on a position of the penetration instrument as determined by determining the position of the penetration instrument, with reliable positional data of the penetration instrument now also being available during the penetration. Using volume image data is particularly advantageous within the scope of the method to the extent that the marking out then is based on data which takes three-dimensional conditions into account, rather than being based on only slice images from which conclusions about the third dimension of the guide line can at best be drawn indirectly.

At least one embodiment is directed to a control device for actuating light emission sources which emit at least two light fan beams. This control device at least comprises the following components:

an input interface for image and/or positional data of an object from an imaging recording system, a processing unit which is designed in such a fashion that it derives a guide line for the penetration of a penetration instrument into the object from the image and/or positional data, a light emission source position determination unit which is designed in such a fashion that it calculates possible positions and radiation directions of the light emission sources from the guide line, from which it is possible to derive an alignment of the light fan beams of the light emission sources, in which a line of intersection of the light fan beams reproduces the guide line, a control command generating unit which is designed in such a fashion that it derives control commands for an actuating device for arranging and aligning the light emission sources using possible positions and radiation alignments of the light emission sources, and at least one output interface for transmitting the control commands to the actuating device, wherein the control device is designed in such a fashion that measurement data for determining the position of the penetration instrument, acquired by the imaging recording system, is used to correct the alignment of the fan beams depending on a position of the penetration instrument as determined by determining the position of the penetration instrument.

A correspondingly designed control device for actuating light emission sources emitting at least two light fan beams can, via the input interface for image and/or positional data of the object, receive corresponding data from the imaging recording system and use this to derive a guide line for the penetration instrument in the processing unit. In the following, the control device calculates the optimum positions and radiation directions of these light emission sources for marking out depending on the basic ability to position the light emission sources. Depending on the variability of the alignment possibilities of the light emission sources, the control device generates corresponding control commands via the output interface to an actuating device for the light emission sources. As a result of this, the light emission sources are aligned in such a fashion that, according to an embodiment of the invention, their fan beams meet at a line of intersection which in turn is coaxial with the penetration direction of the penetration instrument.

Moreover, at least one embodiment of the invention is directed to a marking out apparatus for marking out a guide line in an object for a penetration instrument. This marking out apparatus has a control device according to the invention in addition to at least two light emission sources with an actuating device to position the former, with the light emission sources being designed in such a fashion that, during operation, they emit fan beams and can be aligned in such a fashion that the fan beams can intersect.

At least one embodiment of the invention is directed to an imaging recording system with a marking out apparatus according to the invention attached thereto. In this context, attachment refers to the marking out apparatus being connected directly or indirectly to the imaging recording system. This can mean mechanically fixing the marking out apparatus to the imaging recording system, but also attaching the marking out apparatus at a fixed distance from the imaging recording system. For example, the marking out apparatus can be embodied as a frame fixed at a fixed distance in front of the imaging recording system.

Fixing the marking out apparatus on the recording system ensures that the coordinates of objects determined by the imaging recording system based on image data of the object can be used directly as coordinates for the marking out apparatus and for the penetration of a penetration instrument with the aid of the marking out function of the marking out apparatus. This means that the marking out apparatus according to at least one embodiment of the invention and the imaging system can use the same coordinate system.

Individual elements of the marking out apparatus according to at least one embodiment of the invention, in particular the control apparatus according to the invention, can be implemented either as hardware or using software, or can comprise both hardware and software components. Whereas hardware components are faster during operation, software is more cost-effective, can be varied more flexibly and can be implemented more quickly; this is why a mainly software-technical implementation is sought after. It is for this reason that at least one embodiment of the invention also comprises a computer program product, which can be loaded directly into a processor of a programmable control device for an actuating device, with program code segments in order to execute all steps of a method according to at least one embodiment of the invention, if the program product is executed in the control device.

Further particularly advantageous refinements and developments of the invention also emerge from the dependent claims and the following description. Here, the control device, the marking out apparatus, the imaging recording system and the method can also be developed according to the dependent claims of the respective other claim categories.

Preferably, the light fan beams are emitted in such a fashion that the intersection point of the line of intersection of the light fan beams with the object marks out the penetration point. This means that the fan beams are respectively positioned such that they are incident on the object at the penetration point. This draws a point of intersection on the object, which serves as a starting point for the penetration instrument. Thus, applying the penetration instrument on this starting point and aligning it in the direction of the guide line quickly and effectively ensures that the instrument is positioned correctly and can act in the target direction.

Preferably, the light fan beams are emitted in such a fashion that one end point of the line of intersection of the light fan beams with the object marks out one end point of the guide line. This end point of the guide line can be put level with that end point of the penetration instrument which lies on the opposite side of the penetration instrument that penetrates the object. An end point marking out such as this provides a user with an indication of how far the penetration instrument has to be inserted in order to arrive at the desired target point in the object and advantageously not pass beyond it.

In particular, provision is also made for the light emission sources for the light fan beams to be moved along a movement device which is fitted at a defined distance from a reference plane of the imaging recording system. In principle, any plane of the imaging recording system can be fixed as the reference plane. However, a plane parallel to the front plane of the imaging recording system is preferably used as the reference plane. In this case, the front plane is understood to be the plane which comprises an entry for objects which are inserted into the imaging system for the purposes of imaging. This front plane in general is perpendicular to the insertion direction of these objects.

Such a movement device acts as a type of frame for the object. In the simplest embodiment, the light emission sources are fitted to a vertically erected rod situated next to the object. However, a frame which spans the object in the manner of a bridge is preferable and it, for example, can run like an arc in a semicircle or circle around, or at least transversely across, the object. The movement device in this case thus comprises a frame in the shape of an annular segment which is based on a circle or an ellipse. However, it can also be designed in the manner of a bridge as a frame, comprising straight braces, which is fitted on one or more sides of the object—usually running vertically on both sides of the object and horizontally above the object.

Such a movement device ensures that the light emission sources are fitted at a fixed distance from the imaging recording system and hence the image data from the recording system is able to directly provide the coordinates for marking out by way of the light emission sources. Within the scope of this, it is therefore particularly preferable for measurement data for determining the position of the object to be acquired by the imaging recording system itself.

Furthermore, the movement device is advantageously fixed parallel to an orbit of the imaging recording system. For example, the gantry of a computed tomography scanner, along which the x-ray source rotates about an examination space, is to be understood as an orbit.

A marking out apparatus according to the invention is preferably distinguished by the fact that the light emission sources can be turned and/or tipped into themselves. Thus, their radiation direction can be aligned in different directions and, the more variably they can be moved, the more flexible their marking out possibilities are.

To ensure sufficient accuracy for marking out, provision is advantageously made for firstly the alignment of the light fan beams to be calibrated by way of a test marking out, during which calibration the test marking out is detected by way of the imaging recording system and experimental marking out of the position is carried out by way of the two light fan beams. Here, an intersection point of the line of intersection of the two light fan beams is adjusted to the test marking out. For example, for the purposes of such a calibration, a marking can be fitted to a test object; however, it is also possible to undertake marking out on a bearing device provided for objects. For example, when using a computed tomography scanner as an imaging system, a cross-shaped marking of x-ray impervious material can be fitted. Preferably, at least two such markings are carried out and subsequently calibrated so that the light fan beams can be aligned in a number of directions. This calibration preferably comprises an alignment in all three spatial directions, for the purposes of which the use of at least three markings is advantageous.

Such calibration makes it possible to verify whether the light fan beams are aligned such that they reproduce a penetration direction and a penetration point precisely in such a fashion as is provided on account of an image measurement. The calibration therefore results in a high reliability of the method. Calibration is preferably carried out after defined intervals, particularly preferably before the pass of every marking of an object into which the penetration instrument should penetrate.

It is particularly preferable to use a computed tomography system as an imaging recording system. A computed tomography scanner can generate very fine and precise images of the interior of a multiplicity of objects, whether these are human bodies or inanimate objects. They therefore provide the advantage of a particularly broad field of application.

BRIEF DESCRIPTION OF THE DRAWINGS

The invention will once again be explained in more detail in the following text on the basis of example embodiments with reference to the appended figures. Here, the same components are provided with identical reference numbers in the different figures, in which FIG. 5 shows the marking out apparatus in accordance with FIG. 4 in a lateral sectional view, FIG. 6 shows a third embodiment of a marking out apparatus according to the invention in a top view in the insertion direction of an object into an imaging recording system.

DETAILED DESCRIPTION OF THE EXAMPLE EMBODIMENTS

Figure 1:
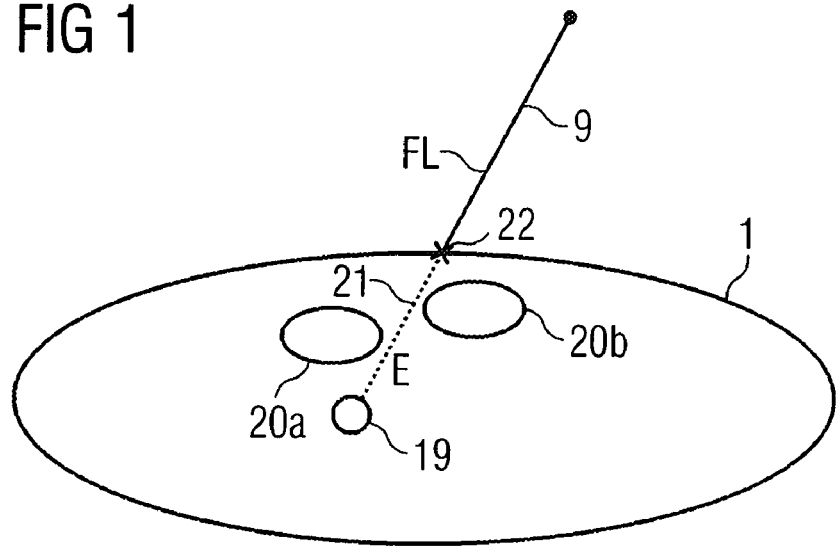
FIG. 1 shows a first schematic sectional view of an object and a penetration instrument.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a section through an object 1, for example a human body with a target object 19 lying therein. This target object 19 may be, for example, a liquid cyst or another organ and it is intended to be pricked by a penetration instrument 9 in the form of a catheter in order to remove liquid. An appropriate slice image (in a less schematic form) can be generated by a suitable imaging method, for example a CT scan. Furthermore, it is possible to determine a penetration channel 21 for the penetration instrument 9, which channel in this case leads directly from a penetration point 22 on the outer covering of the object 1 to the target object 19 in one penetration direction E. The extension of this penetration channel 21 out of the object 1 defines the guide line FL for the penetration instrument 9. The penetration channel 21 in this case is formed between two non-target objects 20a, 20b which must not be touched during the penetration of the penetration instrument 9 and which are, for example, vulnerable organs. The method according to an embodiment of the invention and the corresponding marking out apparatus are intended to assist a user during the penetration of the penetration instrument 9.

In the following figures, example embodiments of the invention are used which, for the sake of simplicity and clarity, are all within the context of a computed tomography scanner as an imaging system. It is for this reason that reference is once again made to the fact that the invention is not limited to applications in the field of computed tomography, but rather that it can be utilized within the context of other imaging recording systems as well. At this point, reference is also made to the fact that the marking out method is not limited to an application in the field of medicine technology. Thus, the object can, for example, also be a historical examination object such as a mummy wrapped in linen from which samples are intended to be taken in a targeted manner using minimally invasive techniques.

Figure 2:
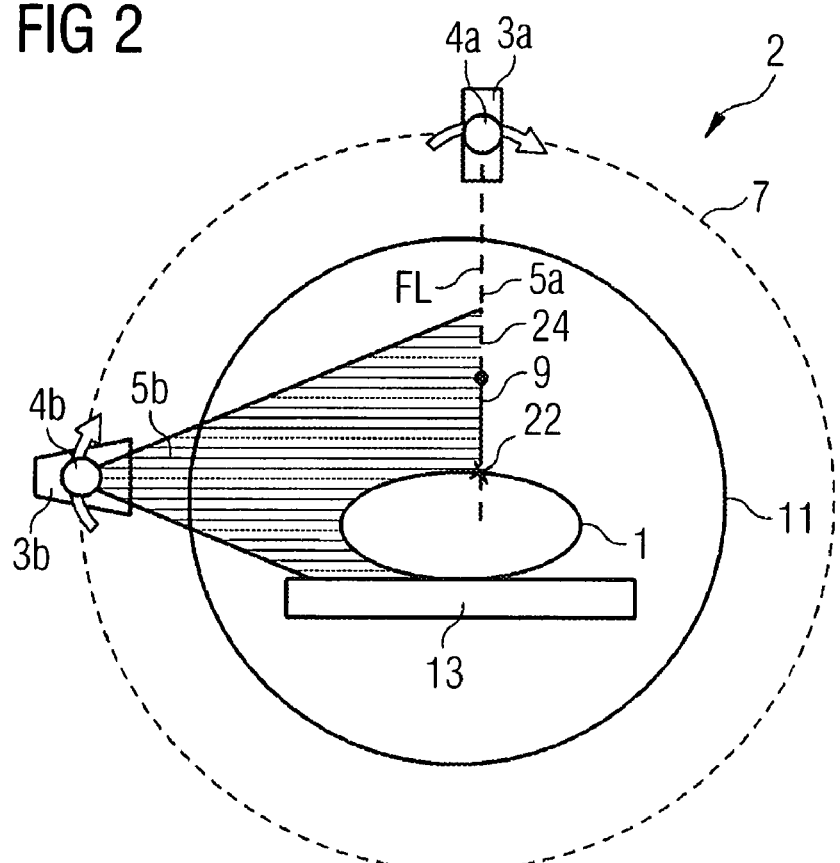
FIG. 2 shows a first embodiment of a marking out apparatus according to the invention in a top view in the insertion direction of an object into an imaging recording system.

FIG. 2 shows a marking out apparatus 2 for marking out a guide line and which is fitted directly in the front of a gantry housing of a computed tomography scanner having a gantry 11. The marking out apparatus 2 comprises two light emission sources 3a, 3b which can be moved along a movement device 7 such that they can be turned or tipped around joints 4a, 4b. The light emission sources 3a, 3b are in this case in the form of fan lasers. The movement device 7 is arranged in an arc-like fashion around the annular opening of the gantry 11.

An object 1 is located on a storage surface which is used as a bearing device 13. An elongate penetration instrument 9 is to be inserted into the object 1.

So as to mark out the guide line FL of the penetration instrument 9 into the object 1, the two fan lasers 3a, 3b emit fan beams. Here, it can be seen that the fan beam 5a of the first fan laser 3a fans open in the line of sight onto the figure, so that it can only be seen as a line, while the second fan beam 5b of the second fan laser 3b is fanned open approximately perpendicularly to the line of sight onto the figure and therefore an approximately V-shaped fan can be seen.

The line of intersection 24 of the two fan beams 5a, 5b defines the guide line FL for the penetration instrument 9. The point at which the two fan beams 5a, 5b are incident on the object 1 is the penetration point 22 for the penetration instrument 9; the further profile of the line of intersection 24 or guide line FL prescribes the penetration direction E of the penetration instrument 9.

A user knows that the penetration instrument 9 is properly aligned with the guide line when the penetration instrument 9 is simultaneously irradiated along its entire length by the two fan beams 5a, 5b. This is because this means that the instrument lies in both fan beam planes. Such irradiation of the penetration instrument 9 is a sign for its correct alignment at least when the penetration instrument 9 has a straight design and the fan beams 5a, 5b each form a plane. However, this principle can also be used when the penetration instrument does not have a straight line shape, for example if it is in the shape of an arc. In this case, at least one of the fan beams must have a corresponding fan shape, for example an arc-shaped bent fan. In this case, in addition to the slightly more complicated alignment of the fan beams in certain directions, the fact that they have to be focused in such a fashion that they image precisely on the penetration instrument in the correct alignment region of the penetration instrument must also be taken into account.

Figure 3:
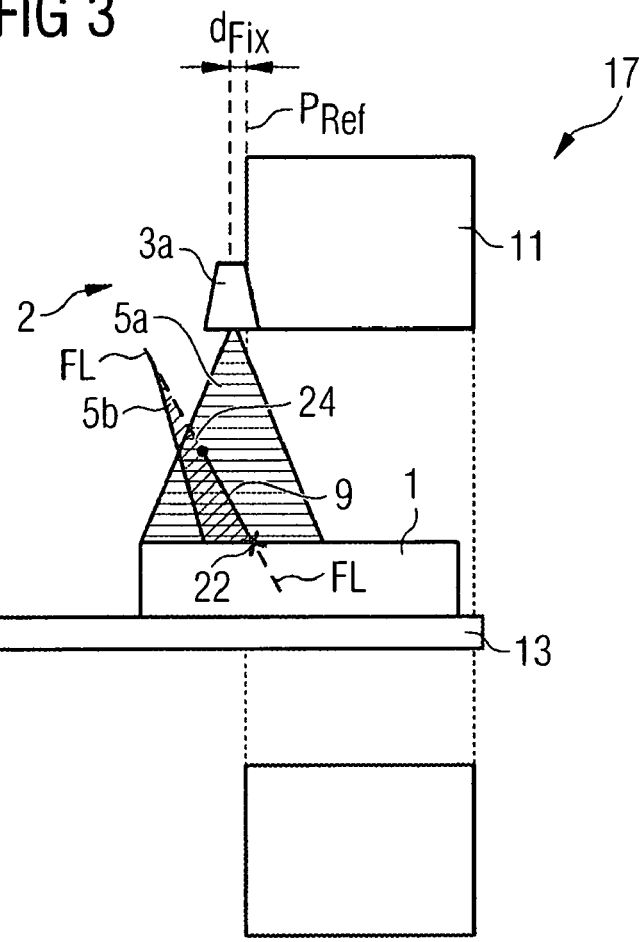
FIG. 3 shows the marking out apparatus in accordance with FIG. 2 in a lateral sectional view.

FIG. 3 shows the same arrangement in a lateral sectional view. The gantry 11, which is part of that computed tomography scanner onto whose one opening side the first fan laser 3a is fitted (in the left-hand side of the figure), can be seen. The second fan laser 3b cannot be seen in the figure since it is behind the first fan beam 5a of the first fan laser 3a. However, both the second fan beam 5b and the penetration instrument 9 are indicated. Furthermore, a reference plane $P_{Ref}$ is defined and in this case, (and in the following examples as well,) it is the same as the plane of the front side of the gantry 11. A fixed distance $d_{Fix}$ can be measured between this reference plane $P_{Ref}$ and the fan laser 3a as a reference point of the marking out apparatus 2; the distance cannot be changed because the marking out apparatus 2 is fixedly attached to the housing of the computed tomography scanner 17.

Figure 4:
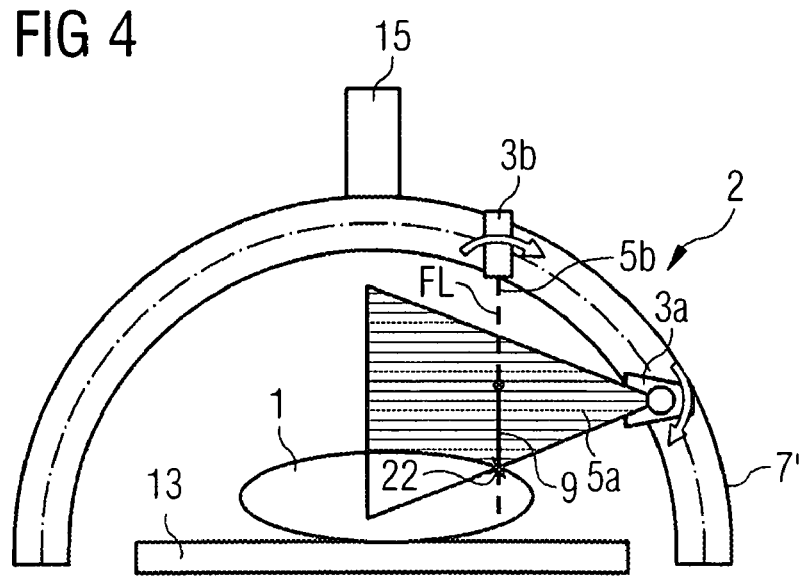
FIG. 4 shows a second embodiment of a marking out apparatus according to the invention in a top view in the insertion direction of an object into an imaging recording system.

FIGS. 4 and 5 respectively illustrate an analog construction as in FIGS. 2 and 3, the difference being that a semicircular frame is used as a movement device 7' and attached to the computed tomography scanner by way of a fixing apparatus 15. This fixing apparatus 15, which is likewise semicircular, is attached to the top side of the gantry housing, and the movement device 7' is hanged on it like a gibbet. Similar constructions of the fixing apparatus 15, for example with a different shape and/or different attachment methods to the computed tomography scanner, are possible.

Figure 7:
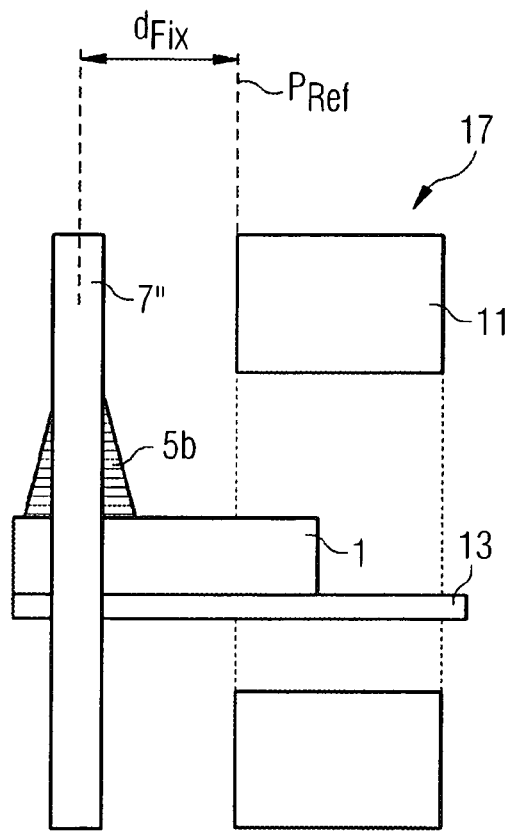
FIG. 7 shows the marking out apparatus in accordance with FIG. 6 in a lateral sectional view.

FIGS. 6 and 7 respectively illustrate a further analog construction as in FIGS. 2 and 3, and 4 and 5, respectively. Here the difference lies in the fact that a frame, comprising two vertical braces and a horizontal transverse brace connecting the two vertical braces, is used as the movement device 7''. It can be seen from FIG. 7 that this frame is also at a fixed, defined distance $d_{Fix}$ from the reference plane $P_{Ref}$ of the computed tomography scanner.

Therefore, the movement devices 7, 7', 7'' are attached to the computed tomography scanner at an unchanging distance $d_{Fix}$ in all three embodiments shown. Additionally, this always puts the light emission sources 3a, 3b at a defined distance which is preferably as short as possible from the reference plane $P_{Ref}$. By contrast, in the other directions they are as freely moveable as possible in order to ensure a large spectrum of changing options.

Figure 8:
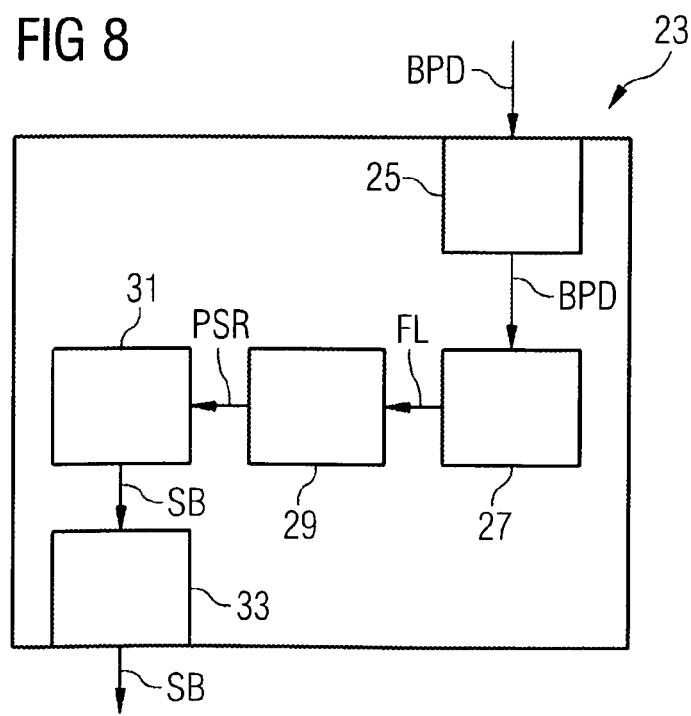
FIG. 8 shows a control device according to the invention in a schematic block diagram.

FIG. 8 shows a control device 23 according to an embodiment of the invention in a schematic block diagram. In this case, it is composed of electronic components, switches or software modules and comprises an input interface 25 for image and/or positional data BPD of an object 1, which data originates from an imaging recording system such as a computed tomography scanner. It outputs control commands SB to an actuating device, for example stepper motors (not illustrated), via an output interface 33 in order to adjust the joints 4a, 4b of fan lasers 3a, 3b.

A processing unit 27, a light emission source position determination unit 29 and a control command generating unit 31 are arranged between these two interfaces. The processing unit 27 derives a guide line FL for the penetration of a penetration instrument 9 into the object 1 from the image and/or positional data BPD. The light emission source position determination unit 29 calculates possible positions and radiation directions PSR of the light emission sources 3a, 3b from this guide line FL. This makes it possible to derive an alignment of the light fan beams 5a, 5b of the light emission sources 3a, 3b in which a line of intersection 24 of the light fan beams 5a, 5b reproduces the guide line FL. Using these positions and radiation directions PSR, the control command generating unit 31 generates control commands for the actuating device for an arrangement and alignment of the light emission sources 3a, 3b which ensures that the line of intersection 24 of the fan beams 5a, 5b emitted by the light emission sources 3a, 3b images the guide line.

Figure 9:
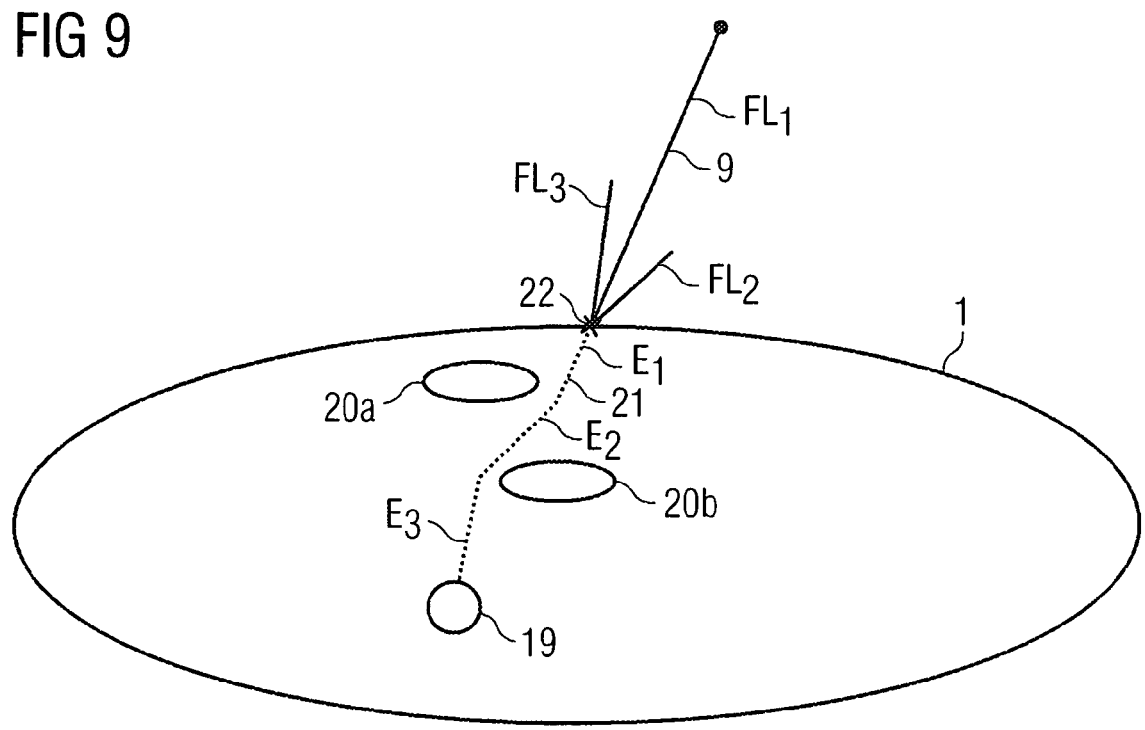
FIG. 9 shows a second schematic sectional view of an object and a penetration instrument.

Hence, a user can very precisely monitor the insertion of the penetration instrument 9 into the object along the penetration channel 21 by way of this guide line FL marked by the fan beams. In this context, FIG. 9 shows an exemplary embodiment of an object 1 with a number of guide lines $FL_1$, $FL_2$, $FL_3$ and having a number of changes in direction. For example, a penetration channel 21 and hence guide lines $FL_1$, $FL_2$, $FL_3$ result when the penetration instrument 9 is prevented from reaching the target object 19 in a straight line by non-target objects 20a, 20b.

It is for this reason that in this case the penetration channel 21 firstly runs in a first penetration direction $E_1$, and then has two further sections in which it runs in different penetration directions $E_2$, $E_3$. The method according to an embodiment of the invention and the corresponding marking out apparatus are intended to assist a user during the penetration of the penetration instrument 9 along these penetration directions $E_1$, $E_2$, $E_3$. To this end, the first guide line $FL_1$ is marked outside of the object 1 during the penetration along the first section of the penetration channel 21. As soon as the end of the first section is reached, the direction has to be changed; this is signaled by marking out the second guide line $FL_2$ on the outside of the object 1. When the third section is reached, the third guide line $FL_3$ is correspondingly marked on the outside of the object 1.

In each case, this is carried out by changing the alignment of the fan beams in accordance with the procedure described above. In this case, the imaging system can be used in a supporting role, for example in order to make the penetration of the penetration instrument 9 traceable. However, the position coordinates of the penetration instrument 9 can also be determined with the aid of other monitoring sensors, for example by way of wireless localization systems. The second and the third guide line $FL_2$, $FL_3$ again run in the direction of the second and third sections of the penetration channel 21, that is to say parallel to the penetration directions $E_2$, $E_3$; however, they are offset in such a fashion that they are incident on the penetration point 22.

Finally, reference is once again made to the fact that the method described in detail above and the illustrated control device and the marking out apparatus equipped therewith are only example embodiments which can be modified by a person skilled in the art in the most diverse fashion without leaving the scope of the invention. Furthermore, use of the indefinite article "a" or "an" does not preclude the possibility of the relevant features being present a number of times.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for marking out a guide line for a penetration instrument entering an object along a penetration channel, the method comprising:
    determining the penetration channel into the object based on image data of the object generated by an imaging recording system, the penetration channel being defined by a penetration point into the object and at least one penetration direction;
    emitting at least two light fan beams from different directions so that a line of intersection of the at least two light fan beams is coaxial with the at least one penetration direction;
    acquiring measurement data for determining a position of the penetration instrument by the image recording system; and
    correcting an alignment of the at least two light fan beams depending on the position of the penetration instrument as determined by determining the position of the penetration instrument.

2. The method as claimed in claim 1, wherein the at least two light fan beams are emitted in such a fashion that the intersection point of the line of intersection of the at least two light fan beams with the object marks out the penetration point.

3. The method as claimed in claim 1, wherein the light at least two light fan beams are emitted in such a fashion that one end point of the line of intersection of the at least two light fan beams with the object marks out one end point of the guide line.

4. The method as claimed in claim 1, wherein light emission sources for the at least two light fan beams are moved along a movement device which is fitted at a defined distance from a reference plane of the imaging recording system.

5. The method as claimed in claim 4, wherein measurement data for determining the position of the object is acquired by the imaging recording system.

6. The method as claimed in claim 1, wherein firstly the alignment of the at least two light fan beams is calibrated by way of a test marking out, during which calibration the test marking out is detected by way of an imaging recording system and experimental marking out of the position is carried out by way of the at least two light fan beams, with an intersection point of the line of intersection of the at least two light fan beams being adjusted to the test marking out.

7. The method as claimed in claim 1, wherein a computed tomography system is used as the imaging recording system.

8. A computer program product including a non-transitory computer-readable medium loadable directly into a processor of a programmable control device for an actuating device, including program code segments to execute the method as claimed in claim 1 when the program product is executed in the programmable control device.

9. The method as claimed in claim 2, wherein the light at least two light fan beams are emitted in such a fashion that one end point of the line of intersection of the at least two light fan beams with the object marks out one end point of the guide line.

10. The method as claimed in claim 2, wherein firstly the alignment of the at least two light fan beams is calibrated by way of a test marking out, during which calibration the test marking out is detected by way of an imaging recording system and experimental marking out of the position is carried out by way of the at least two light fan beams, with an intersection point of the line of intersection of the at least two light fan beams being adjusted to the test marking out.

11. A control device for actuating light emission sources which emit at least two light fan beams, comprising:
  an input interface for at least one of image and positional data of an object from an imaging recording system;
  a processing unit, designed to derive a guide line for a penetration of a penetration instrument into the object from the at least one of image and positional data and designed to acquire measurement data to determine a position of the penetration instrument;
  a light emission source position determination unit, designed to calculate possible positions and radiation directions of the light emission sources from the guide line, from which an alignment of the at least two light fan beams of the light emission sources is derivable, in which a line of intersection of the at least two light fan beams reproduces the guide line, wherein the light emission source position determination unit is designed to correct the alignment of the at least two light fan beams depending on the determined position of the penetration instrument and the acquired measurement data;
  a control command generating unit, designed to derive control commands for an actuating device for arranging and aligning the light emission sources using possible positions and radiation alignments of the light emission sources; and
  at least one output interface for transmitting the control commands to the actuating device.

12. A marking out apparatus for marking out a guide line in an object for a penetration instrument, comprising:
  at least two light emission sources with an actuating device to position the at least two light emission sources, wherein the at least two light emission sources are designed in such a fashion to, during operation, emit fan beams and wherein the at least two light emission sources are alignable such that the fan beams intersect; and
  a control device as claimed in claim 11.

13. The marking out apparatus as claimed in claim 12, wherein the at least two light emission sources are fitted in a moveable fashion along a movement device, fitted at a defined distance from an imaging recording system.

14. The marking out apparatus as claimed in claim 13, wherein the movement device comprises a bridge-like frame.

15. The marking out apparatus as claimed in claim 12, wherein the at least two light emission sources are at least one of turnable and tipable into themselves.

16. An imaging recording system comprising a marking out apparatus as claimed in claim 12 attached thereto.

17. The recording system as claimed in claim 16, wherein a movement device is attached parallel to an orbit of the imaging recording system, with the light emission sources being fitted in a moveable fashion along the movement device which is fitted at a defined distance from an imaging recording system.

18. The marking out apparatus as claimed in claim 13, wherein the at least two light emission sources are at least one of turnable and tipable into themselves.

19. An imaging recording system comprising a marking out apparatus as claimed in claim 13 attached thereto.

20. A control device for actuating light emission sources which emit at least two light fan beams, comprising:
  means for determining the penetration channel into the object based on image data of the object generated by an imaging recording system, the penetration channel being defined by a penetration point into the object and at least one penetration direction;
  means for emitting at least two light fan beams from different directions so that a line of intersection of the at least two light fan beams is coaxial with the at least one penetration direction;
  means for acquiring measurement data for determining a position of the penetration instrument; and
  means for correcting an alignment of the at least two light fan beams depending on the position of the penetration instrument as determined by determining the position of the penetration instrument.

* * * * *